United States Patent [19]

Drabb

[11] 4,439,607

[45] Mar. 27, 1984

[54] METHOD FOR THE PREPARATION OF CERTAIN PYRIDINE AND QUINOLINE 2,3-DICARBOXYLIC ANHYDRIDES

[75] Inventor: Thomas W. Drabb, Trenton, N.J.

[73] Assignee: American Cyanamid Company, Stamford, Conn.

[21] Appl. No.: 381,816

[22] Filed: May 25, 1982

[51] Int. Cl.$^3$ ................. C07D 491/048; C07D 498/04
[52] U.S. Cl. ........................................ 546/89; 546/116
[58] Field of Search .................................. 546/116, 89

[56] References Cited

U.S. PATENT DOCUMENTS

3,825,535  7/1974  Denzel et al. ...................... 546/116

*Primary Examiner*—Henry R. Jiles
*Assistant Examiner*—Robert C. Whittenbaugh
*Attorney, Agent, or Firm*—H. G. Jackson

[57] ABSTRACT

The present invention relates to a process for the preparation of substituted pyridine and quinoline-2,3-dicarboxylic anhydrides, and the herbicidally effective imidazolinyl pyridine and quinoline compounds prepared therefrom.

5 Claims, No Drawings

METHOD FOR THE PREPARATION OF CERTAIN PYRIDINE AND QUINOLINE 2,3-DICARBOXYLIC ANHYDRIDES

SUMMARY OF THE INVENTION

The present invention relates to a process for the preparation of certain substituted pyridine and quinoline-2,3-dicarboxylic anhydrides having the structure (I)

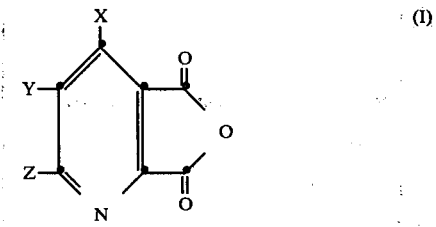

wherein X is hydrogen, halogen or methyl, with the proviso that when Y and Z are taken together to form a ring and YZ is represented by the structure: $-(CH_2)_n-$, where n is 3 or 4, then X is hydrogen; Y and Z each represent members selected from the group consisting of hydrogen, halogen, $C_1-C_6$ alkyl, $C_1-C_6$ alkoxy, $C_1-C_4$ alkylthio, phenoxy, $C_1-C_4$ haloalkyl, nitro, cyano, $C_1-C_4$ alkylsulfonyl group, or phenyl optionally substituted with one $C_1-C_4$ alkyl, $C_1-C_4$ alkoxy or halogen; and, when taken together, Y and Z may form a ring in which —(YZ)— is represented by the structure: $-(CH_2)_n-$, where n is an integer selected from 3 and 4, provided that X is hydrogen; or —(YZ)— is

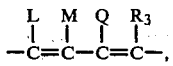

where L, M, Q and $R_3$ each represent members selected from the group consisting of hydrogen, halogen, $C_1-C_4$ alkyl, $C_1-C_4$ alkoxy, $C_1-C_4$ alkylthio, $C_1-C_4$ alkylsulfonyl, $C_1-C_4$ haloalkyl, $NO_2$, CN, phenyl, phenoxy, chlorophenyl, methylphenyl, or phenoxy substituted with one Cl, $CF_3$, $NO_2$ or $CH_3$ group, with the proviso that only one of L, M, Q or $R_3$, may represent a substituent other than hydrogen, halogen, $C_1-C_4$ alkyl or $C_1-C_4$ alkoxy; which are useful as intermediates in the manufacture of the herbicidally effective 2-(2-imidazolin-2-yl)pyridine compounds described in the application for United States Letter Patent of Marinus Los, Ser. No. 382,041, filed concurrently herewith and incorporated herein by reference thereto. The compounds of the Los application are illustrated by formula (II) below:

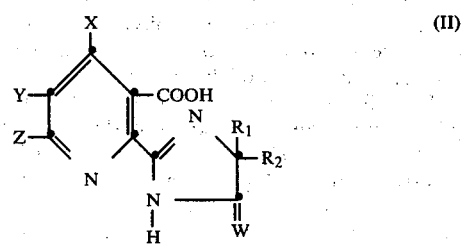

wherein $R_1$ is $C_1-C_4$ alkyl; $R_2$ is $C_1-C_4$ alkyl or $C_3-C_6$ cycloalkyl; and when $R_1$ and $R_2$ are taken together they may represent $C_3-C_6$ cycloalkyl optionally substituted with methyl; W is O or S; X is hydrogen, halogen or methyl, with the proviso that when Y and Z are taken together to form a ring and YZ is represented by the structure: $-(CH_2)_n-$, where n is 3 or 4, then X is hydrogen; Y and Z each represent members selected from the group consisting of hydrogen, halogen, $C_1-C_6$ alkyl, $C_1-C_6$ alkoxy, $C_1-C_4$ alkylthio, phenoxy, $C_1-C_4$ haloalkyl, nitro, cyano, $C_1-C_4$ alkylsulfonyl group, or phenyl optionally substituted with one $C_1-C_4$ alkyl, $C_1-C_4$ alkoxy or halogen; and, when taken together, Y and Z may form a ring in which —(YZ)— is represented by the structure: $-(CH_2)_n-$, where n is an integer selected from 3 and 4, provided that X is hydrogen; or —(YZ)— is

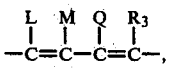

where L, M, Q and $R_3$ each represent members selected from the group consisting of hydrogen, halogen, $C_1-C_4$ alkyl, $C_1-C_4$ alkoxy, $C_1-C_4$ alkylthio, $C_1-C_4$ alkylsulfonyl, $C_1-C_4$ haloalkyl, $NO_2$, CN, phenyl, phenoxy, chlorophenyl, methylphenyl, or phenoxy substituted with one Cl, $CF_3$, $NO_2$ or $CH_3$ group, with the proviso that only one of L, M, Q or $R_3$, may represent a substituent other than hydrogen, halogen, $C_1-C_4$ alkyl or $C_1-C_4$ alkoxy, the salts thereof, and when $R_1$ and $R_2$ are different the racemates and optical isomers thereof.

The process of the invention involves reaction of a formula (III) dicarboxylic acid

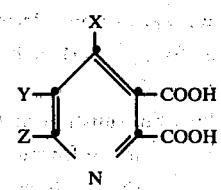

wherein X, Y and Z are as hereinabove defined with equimolar or excess amounts of phosgene in the presence of a suitable, inert solvent, and small amounts of dimethylformamide used to promote the reaction. Conveniently, the above reaction may be run at a broad temperature range for a period of time sufficient to complete the reaction. This reaction sequence may be graphically illustrated, as follows:

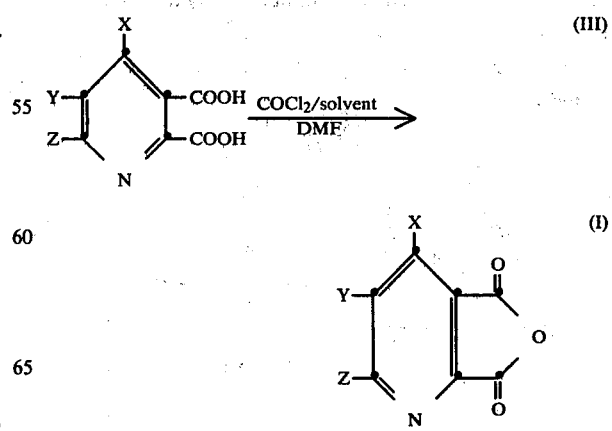

As indicated above, the anhydrides of formula (I) are useful and valuable intermediates for the preparation of formula (II) herbicides.

Thus, reaction of the formula (I) substituted pyridine (quinoline)-2,3-dicarboxylic anhydride with an aminocarboxamide of formula (IV) or an aminothiocarboxamide of formula (IV), preferably in the presence of an organic solvent such as tetrahydrofuran (THF), under a blanket of an inert gas such as nitrogen, yields the corresponding isomeric mixture of monoacid-monoamide products illustrated by formula (VI) and (VII).

The solvent is then removed under vacuum and the residue containing the isomeric monoacid-monoamide products is dissolved in strong base, such as 6 N sodium hydroxide. The thus-formed mixture is then heated to a temperature between about 50° and 100° C. and preferably between 60° and 80° C., with or without a blanket of inert gas such as nitrogen. The mixture is cooled and the pH thereof adjusted to between pH 8 and 10 and preferably to pH 8.5 to 9.5 with a strong mineral acid such as sulfuric acid. The reaction mixture is extracted with an organic solvent such as ether and the organic extracts discarded. The aqueous phase is then adjusted to a pH between about 2 and 4 and preferably about pH 3 with a strong mineral acid such as sulfuric acid. The resulting precipitate is removed by any convenient means, such as filtration, washed with water and dried to give the herbicidally effective formula (I) substituted 2-(2-imidazolin-2-yl)nicotinic acid.

By the same procedure, but substituting the appropriate aminothiocarboxamide for the formula (IV) aminocarboxamide, one obtains the herbicidally effective thiono derivative of the substituted 2-(2-imidazolin-2-yl)nicotinic acid.

The above-described base-catalyzed cyclization of the formula (VI) and (VII) substituted 2,3-pyridinedicarboxylic acid monoamides is described in the application for United States Letters Patent of Jerry Michael Barton, Don Wesley Long and Kenneth Dale Lotts, Ser. No. 381,818, filed concurrently herewith and incorporated herein by reference thereto.

This base-catalyzed cyclization is graphically illustrated below:

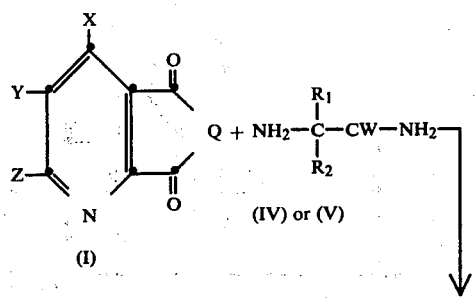

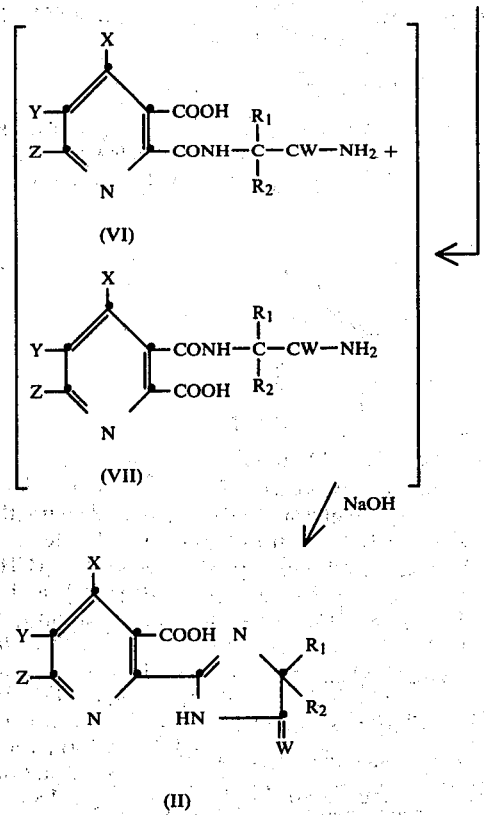

wherein W, X, Y, Z, $R_1$ and $R_2$ are as hereinabove defined.

Thus, one molar equivalent of a formula (III) acid is admixed with an inert solvent selected from a group consisting of aliphatic and aromatic hydrocarbons, lower alkyl and halogen substituted aromatic hydrocarbons, alkylnitriles, ethers and the like and mixtures thereof, and in the presence of from about 0.05 molar equivalent to about 0.75 molar equivalent, and preferably from about 0.2 to about 0.4 molar equivalent of DMF, then about 1 to about 6 molar equivalents and preferably 1 to 2 molar equivalents of phosgene is added either as a preprepared solution of phosgene in the solvent selected, or induced as a gas (or liquid) under the surface of the reaction mixture at a temperature of from about $-5°$ C. to about $+50°$ C., and preferably from about $+15°$ C. to about $+25°$ C. for a period of time from about one hour to about 12 hours, preferably 2 to 5 hours, or until the reaction is essentially complete. On completion of the reaction the excess phosgene (if any) is removed from the reaction mixture, as by under reduced pressure, and the solution of the anhydrides used as is, or, if so desired, the anhydride may be isolated from the reaction mixture by conventional methods, such as evaporation of the solvent.

The formula (II) substituted 2-(2-imidazolin-2-yl)nicotinic acids are effective herbicidal agents useful for the control of a wide variety of herbaceous and woody annual and perennial monocotyledonous and dicotyledonous plants. Moreover, these compounds are herbicidally effective for controlling weeds indigenous to both dry land and wet land areas. They are also useful as aquatic herbicides and are unique in their effectiveness in controlling the above-said plants when applied to the foliage thereof or to soil or water containing seeds or other propagating organs of said plants such as tubers, rhizomes or stolons, at rates of from about 0.025 to 8.0 kg/ha.

The formula (II) substituted 2-(2-imidazolin-2-yl)nicotinic acids can be formulated as wettable powders, flowable concentrates, emulsifiable concentrates, granular formulations and the like for application to undesirable plant species for the control thereof.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butylcellosolve, methylacetate or the like and dispersing therein about 5% to 10% by weight of a nonionic surfactant such as alkylphenoxy polyethoxy alcohol. This concentrate is dispersed in water for application as a liquid spray.

When the compounds of formula (II) are to be used as herbicides where soil treatments are involved, the compounds may be prepared and applied as granular products. Preparation of such a granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims.

EXAMPLE 1

Preparation of quinoline-2,3-dicarboxylic anhydrides

To a stirred mixture of 4.7 g (0.02 mol) of quinoline-2,3-dicarboxylic acid monohydrate, 75 ml of acetonitrile and 0.5 ml of dimethylformamide (DMF) is added, dropwise, 17.4 g (0.022 mol) of a 12.5% solution of phosgene in toluene at 20° C. Next, the mixture is stirred at room temperature for 2 to 3 hours and then the solvent is evaporated to afford 4.0 g of a cream solid, mp 218°–221° C. The structure of the product is confirmed by an infrared spectrum.

By the above method, and starting with the corresponding dicarboxylic acids the following anhydrides are obtained:

| Compound | mp °C. |
|---|---|
| CH$_3$O-/CH$_3$O- substituted | 266–267 |
| CH$_3$S- substituted | 247–251 |
| NC- substituted | 190–192 |

EXAMPLE 2

Preparation of pyridine-2,3-dicarboxylic anhydrides

By the method of Example 1, the following anhydrides are prepared.

| X | Y | Z | mp °C. |
|---|---|---|---|
| H | H | H | 135–137 |
| H | H | Cl-phenyl | solid |
| H | H | CH$_3$-phenyl | solid |
| H | H | C$_2$H$_5$- | 65–67 |
| H | H | C$_3$H$_7$- | oil |
| H | H | —iso-C$_3$H$_7$— | oil |
| H | H | CF$_3$— | oil |
| H | H | CH$_3$— | 106–108.5 |
| H | | —(CH$_2$)$_3$— | semisolid |
| H | CH$_3$— | CH$_3$— | semisolid |

EXAMPLE 3

Preparation of 2-amino-2,3-dimethylbutyramide

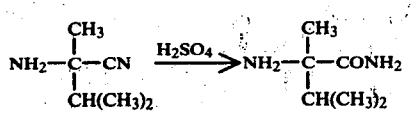

To concentrated sulfuric acid (29.7 ml), cooled with stirring in an ice-acetone cooling bath, is added 11.8 g (−)-2-amino-2,3-dimethylbutyronitrile with $[\alpha]_D^{25} = 7.31°$ (c=0.0368 g/ml THF) at such a rate that the temperature does not go above 25° C. After the addition, the temperature of the reaction mixture is slowly raised to 100° C. and held at that temperature for one hour. After cooling the mixture in an ice-acetone bath, 85 ml concentrated ammonium hydroxide is added at such a rate that the temperature does not exceed 75° C. The mixture is extracted five times with methylene chloride, the combined extracts dried and concentrated. This gives 11.95 g of white solid, mp 79°–81° C. and $[\alpha]_D^{25} = +57.43°$ (c=0.0213 g/ml THF). This solid is recrystallized from methylene chloride-hexane to give 11.2 g of (+)-2-amino-2,3-dimethylbutyramide, mp 81°–82° C. $[\alpha]_D^{25} = +59.38°$ (c=0.0162 g/ml THF).

In a similar way, hydrolysis of the (+)-2-amino-2,3-dimethylbutyronitrile with sulfuric acid yields the (−)-2-amino-2,3-dimethylbutyramide, mp 81°–82° C., $[\alpha]_D^{25} = -57.14°$ (c=0.0654 g/ml THF).

In a similar way, hydrolysis of the (+)-2-amino-2,3-dimethylbutyronitrile with sulfuric acid yields (+)-2-amino-2,3-dimethylbutyramide, mp 74.5°–76° C.

EXAMPLE 4

Preparation of 2-amino-2,3-dimethylthiobutyramide

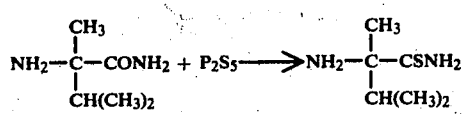

A stirred mixture containing 39 g of 2-amino-2,3-dimethylbutyramide and 73.3 g phosphorus pentasulfide in 1 L dry dioxane is heated at reflux for four hours. After stirring at room temperature for 72 hours, the mixture is again heated at reflux for two hours, the mixture is cooled, concentrated, and the residue distributed between water and methylene chloride. The aqueous phase is separated, the pH adjusted to 8 with concentrated ammonium hydroxide and extracted three times with methylene chloride. All the organic phases were combined, dried and concentrated to give 22.47 g product, mp 78°–85° C. Recrystallization of this material first from ethyl acetate and then methylene chloride-pentane gives analytically pure 2-amino-2,3-dimethylthiobutyramide with mp 98°–100° C.

EXAMPLE 5

Preparation of 6-isopropyl-2-(5-isopropyl-5-methyl-4-oxo-2-imidazolin-2-yl)nicotinic acid

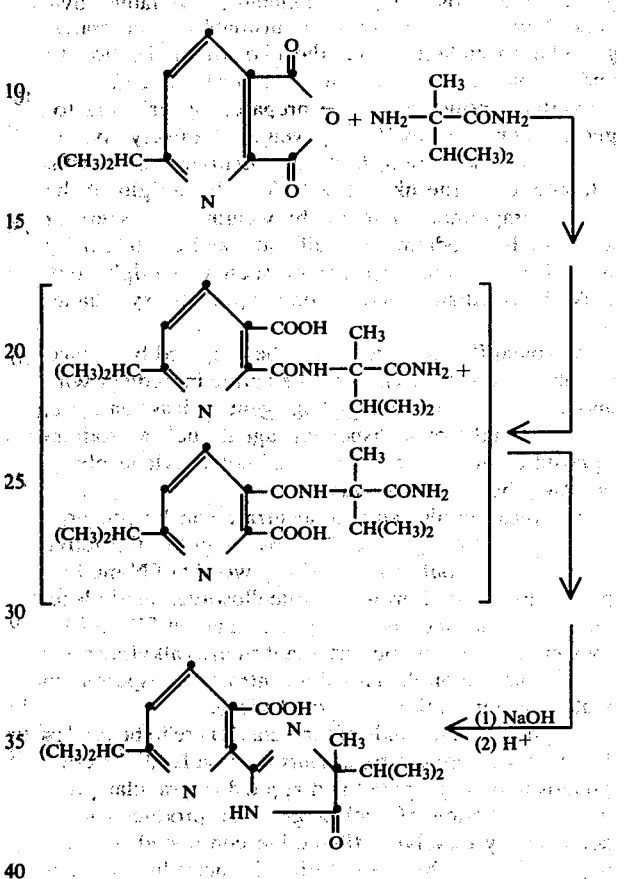

To a stirred solution of the anhydride (15.1 g) in 125 ml THF under nitrogen is added 11.4 g of 2-amino-2,3-dimethylbutyramide. The mixture is stirred overnight. The solvent is removed in vacuo; and the resulting oil (consisting of a mixture of the isomeric pyridine monoacid-monoamide products) dissolved in 66 ml of 6 N NaOH. This solution is heated at 70° C. under nitrogen for three and one-half hours, then cooled and the pH of the solution adjusted to 9 with 6 N $H_2SO_4$. The mixture is extracted twice with ether, and the organic extracts discarded. The aqueous phase is adjusted to pH 3 with 6 N $H_2SO_4$. The resulting precipitate is removed by filtration, washed with water and dried to give 13.25 g of desired product. A sample is recrystallized from methylene chloride-hexane followed by ether-hexane to give an analytically pure sample of 6-isopropyl-2-(5-isopropyl-5-methyl-4-oxo-2-imidazolin-2-yl)nicotinic acid, mp 131°–133.5° C.

By using essentially the same procedure but substituting the appropriate substituted 2,3-pyridinedicarboxylic anhydride for 6-isopropyl-2,3-pyridinedicarboxylic anhydride and also substituting, if necessary, the optically active 2-amino-2,3-dimethylbutyramide or the 2-amino-2,3-dimethylthiobutyramide for 2-amino-2,3-dimethylbutyramide, the following nicotinic acids were prepared.

[Structure 1: pyridine with X, Y, Z substituents, COOH, and imidazolinone side chain containing CH3, CH(CH3)2, HN, C=O]

| X | Y | Z | mp °C |
|---|---|---|---|
| H | H | CH₃ | 145–146.5 |
| H | H | CF₃ | 133–142 |
| H | H | H | 128–131 $[\alpha]_D^{25} = +18.37°$ (c = 0.0902 g/ml THF) |
| H | H | C₃H₇ | 148.5–150.5 |
| H | H | (4-Cl-phenyl) | 247–249 |
| H | H | (4-CH₃-phenyl) | 215.5–218.5 |
| H | H | (phenyl) | 252–254 |
| H | H | C₂H₅ | 118–122 |
| H | CH₃ | CH₃ | 172–180 |
| H | —(CH₂)₃— | | 160–164 |
| H | H | H | 170–172.5 |
| H | —(CH₂)₄— | | 162–165 | and

[Structure 2: pyridine-COOH with imidazoline-thione side chain: CH₃, CH(CH₃)₂, HN, C=S]

mp 182–184 °C

EXAMPLE 6

Postemergence herbicidal evaluation of test compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 actone/water mixtures containing 0.5% TWEEN ® 20, a polyoxyethylene sorbitan monolaurate surfactant of Atlas Chemical Industries, in sufficient quantity to provide the equivalent of about 0.025 kg to 8 kg per hectare of active compound when applied to the plants through a spray nozzle operating at 2.8 kg cm$^{-2}$ pressure for a predetermined time. After spraying, the plants are placed on greenhouse benches and are cared for in the usual manner, commensurate with conventional greenhouse practices. From 4 to 5 weeks after treatment, the seedling plants are examined and rated according to the rating system provided below. The data obtained are recorded in Table I below.

| Rating System | % Difference in Growth from the Check* |
|---|---|
| 0 No effect | 0 |
| 1 Possible effect | 1–10 |
| 2 Slight effect | 11–25 |
| 3 Moderate effect | 26–40 |
| 5 Definite injury | 41–60 |
| 6 Herbicidal effect | 61–75 |
| 7 Good herbicidal effect | 76–90 |
| 8 Approaching complete kill | 91–99 |
| 9 Complete kill | 100 |
| 4 Abnormal growth, that is, a definite physiological malformation but with an overall effect less than a 5 on the rating scale. | |

In most cases the data are for a single test, but in several instances, they are average values obtained from more than one test.

| Plant Species Used | |
|---|---|
| Barnyardgrass | (Echinochloa crusgalli) |
| Green foxtail | (Setaria viridis) |
| Purple nutsedge | (Cyperus rotundus L.) |
| Wild oats | (Avena fatua) |
| Quackgrass | (Agropyron repens) |
| Field bindweed | (Convolvulus arvensis L.) |
| Morningglory | (Ipomoea purpurea) |
| Ragweed | (Ambrosia artemisiifolia) |
| Velvetleaf | (Abutilon theophrasti) |
| Barley | (Hordeum vulgare) |
| Corn | (Zea mays) |
| Rice | (Oryza sativa) |
| Soybean | (Glycine max) |
| Sunflower | (Helianthus annus) |
| Wheat | (Triticum aestivum) |

TABLE I

POST-EMERGENCE TESTS - RATES IN KG/HA

| Compound | RATE | BARNY ARDGR | GREEN FOX | P NUT SEDGE | WILD OATS | QUACK GRASS | FLD B INDWD | MRNGL RY SP | RAGWE ED | VELVE TLEAF | S BAR LY LA |
|---|---|---|---|---|---|---|---|---|---|---|---|
| 2-(5-Isopropyl-5- | 10.000 | 9.0 | 9.0 | 9.0 | 9.0 | | | 7.0 | 9.0 | 9.0 | |
| methyl-4-oxo-2- | 2.000 | 9.0 | 9.0 | 9.0 | 9.0 | | | 8.0 | 8.0 | 9.0 | |
| imidazolin-2-yl)- | 1.000 | 9.0 | 9.0 | 9.0 | 9.0 | 9.0 | 8.8 | 8.8 | 8.8 | 9.0 | 9.0 |
| nicotinic acid | .500 | 9.0 | 9.0 | 8.7 | 9.0 | 9.0 | 9.0 | 8.8 | 8.6 | 8.9 | 9.0 |
| | .250 | 8.9 | 9.0 | 8.8 | 9.0 | 9.0 | 9.0 | 8.9 | 8.6 | 8.9 | 9.0 |
| | .125 | 9.0 | 9.0 | 8.4 | 9.0 | 8.9 | 8.9 | 8.9 | 7.4 | 8.9 | 9.0 |
| (+)-2-(5-Iso- | 1.000 | 9.0 | 9.0 | 9.0 | 9.0 | 9.0 | 9.0 | 9.0 | 9.0 | 9.0 | 9.0 |
| propyl-5-methyl- | .500 | 9.0 | 9.0 | 9.0 | 9.0 | 9.0 | 9.0 | 9.0 | 9.0 | 9.0 | 9.0 |
| 4-oxo-2-imida- | .250 | 9.0 | 9.0 | 9.0 | 9.0 | 9.0 | 9.0 | 9.0 | 9.0 | 9.0 | 9.0 |
| zolin-2-yl)- | .125 | 9.0 | 9.0 | 9.0 | 9.0 | 9.0 | 9.0 | 9.0 | 9.0 | 9.0 | 9.0 |
| nicotinic acid | | | | | | | | | | | |
| 2-(5-Isopropyl- | 4.000 | 9.0 | 9.0 | 7.0 | 9.0 | 9.0 | 9.0 | 6.0 | 6.0 | 7.0 | |

TABLE I-continued

POST-EMERGENCE TESTS - RATES IN KG/HA

| Compound | Rate | | | | | | | | | |
|---|---|---|---|---|---|---|---|---|---|---|
| 5-methyl-4-oxo-2-imidazolin-2-yl)-6-phenyl-nicotinic acid | 1.000 | 9.0 | 9.0 | 3.0 | 7.0 | 2.0 | 6.0 | 4.0 | 4.0 | 2.0 |
|  | .500 | 8.0 | 9.0 | 3.0 | 3.0 |  | 8.0 | 3.0 | 1.0 | 2.0 |
|  | .250 | 8.0 | 7.0 | 2.0 | 2.0 | 2.0 | 5.0 | 1.0 | 0.0 | 0.0 |
| 2-(5-Isopropyl-5-methyl-4-oxo-2-imidazolin-2-yl)-6-methyl-nicotinic acid | 4.000 | 9.0 | 9.0 | 9.0 | 9.0 | 9.0 | 9.0 | 9.0 | 9.0 | 9.0 |
|  | 1.000 | 9.0 | 9.0 | 9.0 | 9.0 | 9.0 | 9.0 | 9.0 | 9.0 | 9.0 |
|  | .500 | 9.0 | 9.0 | 9.0 | 9.0 | 9.0 | 9.0 | 9.0 | 8.5 | 9.0 |
|  | .250 | 9.0 | 9.0 | 9.0 | 9.0 | 9.0 | 9.0 | 9.0 | 7.0 | 9.0 |
|  | .125 | 9.0 |  | 8.0 | 9.0 | 9.0 |  | 9.0 | 5.0 | 9.0 |
| 2-(5-Isopropyl-5-methyl-4-thiono-2-imidazolin-2-yl)nicotinic acid | 1.000 | 9.0 |  | 9.0 | 9.0 | 9.0 | 9.0 | 9.0 | 9.0 | 9.0 |
|  | .500 | 9.0 |  | 9.0 | 9.0 | 9.0 | 9.0 | 9.0 | 9.0 | 9.0 |
|  | .250 | 9.0 |  | 9.0 | 9.0 | 9.0 | 9.0 | 9.0 | 9.0 | 9.0 |
|  | .125 | 8.0 |  | 8.0 | 9.0 | 9.0 | 9.0 | 9.0 | 7.0 | 9.0 |
| 6-Ethyl-2-(5-isopropyl-5-methyl-4-oxo-2-imidazolin-2-yl)nicotinic acid | .250 | 8.0 |  | 9.0 | 8.0 | 9.0 | 9.0 | 9.0 | 5.0 | 8.0 |
|  | .125 | 8.0 |  | 7.0 | 5.0 | 8.0 | 9.0 | 8.0 | 3.0 | 3.0 |
| 2-(5-Isopropyl-5-methyl-4-oxo-2-imidazolin-2-yl)-6-propylnicotinic acid | 1.000 | 9.0 |  | 8.0 | 9.0 | 9.0 | 8.0 | 9.0 | 9.0 | 9.0 |
|  | .500 | 8.0 |  | 7.0 | 8.0 | 9.0 | 9.0 | 9.0 | 8.0 | 9.0 |
|  | .250 | 8.0 |  | 7.0 | 7.0 | 9.0 | 9.0 | 8.0 | 3.0 | 3.0 |
|  | .125 | 8.0 |  | 4.0 | 3.0 | 7.0 | 6.0 | 5.0 | 1.0 | 3.0 |

| Compound | RATE | CORN FIELD | RICE, NATO | SOYBEAN WI | SUNFL R XXX | S WHEAT ER |
|---|---|---|---|---|---|---|
| 2-(5-Isopropyl-5-methyl-4-oxo-2-imidazolin-2-yl)-nicotinic acid | 10.000 |  |  |  |  |  |
|  | 2.000 | 9.0 | 9.0 | 9.0 |  |  |
|  | 1.000 | 9.0 | 9.0 | 9.0 | 9.0 | 9.0 |
|  | .500 | 9.0 | 8.8 | 9.0 | 9.0 | 9.0 |
|  | .250 | 9.0 | 8.8 | 9.0 | 9.0 | 9.0 |
|  | .125 | 9.0 | 8.7 | 8.7 | 9.0 | 9.0 |
| (+)-2-(5-Isopropyl-5-methyl-4-oxo-2-imidazolin-2-yl)-nicotinic acid | 1.000 | 9.0 | 9.0 |  | 9.0 | 9.0 |
|  | .500 | 9.0 | 9.0 |  | 9.0 | 9.0 |
|  | .250 | 9.0 | 9.0 |  | 9.0 | 9.0 |
|  | .125 | 9.0 | 9.0 |  | 9.0 | 9.0 |
| 2-(5-Isopropyl-5-methyl-4-oxo-2-imidazolin-2-yl)-6-phenyl-nicotinic acid | 4.000 | 9.0 | 8.0 |  | 9.0 | 4.0 |
|  | 1.000 | 9.0 | 4.0 |  | 9.0 | 2.0 |
|  | .500 | 6.0 |  |  | 9.0 | 2.0 |
|  | .250 | 6.0 | 3.0 |  | 9.0 | 1.0 |
| 2-(5-Isopropyl-5-methyl-4-oxo-2-imidazolin-2-yl)-6-methyl-nicotinic acid | 4.000 | 9.0 | 9.0 |  | 9.0 | 9.0 |
|  | 1.000 | 9.0 | 9.0 |  | 9.0 | 9.0 |
|  | .500 | 9.0 | 9.0 |  | 9.0 | 9.0 |
|  | .250 | 9.0 | 8.0 |  | 9.0 | 9.0 |
|  | .125 | 9.0 | 7.0 |  | 9.0 | 9.0 |
| 2-(5-Isopropyl-5-methyl-4-thiono-2-imidazolin-2-yl)nicotinic acid | 1.000 | 9.0 | 9.0 |  | 9.0 | 9.0 |
|  | .500 | 9.0 | 9.0 |  | 9.0 | 9.0 |
|  | .250 | 9.0 | 9.0 |  | 9.0 | 9.0 |
|  | .125 | 9.0 | 9.0 |  | 9.0 | 9.0 |
| 6-Ethyl-2-(5-isopropyl-5-methyl-4-oxo-2-imidazolin-2-yl)nicotinic acid | .250 | 9.0 | 8.0 |  | 9.0 | 6.0 |
|  | .125 | 9.0 | 7.0 |  | 9.0 | 4.0 |
| 2-(5-Isopropyl-5-methyl-4-oxo-2-imidazolin-2-yl)-6-propylnicotinic acid | 1.000 | 9.0 | 9.0 |  | 9.0 | 9.0 |
|  | .500 | 9.0 | 9.0 |  | 9.0 | 9.0 |
|  | .250 | 9.0 | 8.0 |  | 9.0 | 8.0 |
|  | .125 | 9.0 | 6.0 |  | 9.0 | 6.0 |

EXAMPLE 7

Pre-emergence herbicidal evaluation of test compounds

The pre-emergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.025 to 8 kg per hectare of test compound per cup. The treated cups are then placed on greenhouse benches, watered and cared for in accordance with conventional greenhouse procedures. From 4 to 5 weeks after treatment, the tests are terminated and each cup is examined and rated according to the rating system set forth above. The herbicidal proficiency of the active ingredients of the present invention is evident form the test results which are recorded in Table II below. Where more than one test is involved for a given compound, the data are averaged.

TABLE II

PRE-EMERGENCE TESTS - RATES IN KG/HA

| | BARNY | GREEN | P NUT | WILD | QUACK | FLD B | MRNGL | RAGWE | VELVE | S BAR |
|---|---|---|---|---|---|---|---|---|---|---|

TABLE II-continued
PRE-EMERGENCE TESTS - RATES IN KG/HA

| Compound | RATE | ARDGR | FOX | SEDGE | OATS | GRASS | INDWD | RY SP | ED | TLEAF | LY LA |
|---|---|---|---|---|---|---|---|---|---|---|---|
| 2-(5-Isopropyl-5-methyl-4-oxo-2-imidazolin-2-yl)-nicotinic acid | 10.000 | 8.0 | 9.0 | 9.0 | 8.0 | | | 8.0 | 8.0 | 8.0 | |
| | 2.000 | 9.0 | 9.0 | 9.0 | 9.0 | | | 8.0 | 9.0 | 9.0 | |
| | 1.000 | 9.0 | 9.0 | 9.0 | 9.0 | 9.0 | 9.0 | 8.0 | 9.0 | 9.0 | 9.0 |
| | .500 | 9.0 | 9.0 | 9.0 | 9.0 | 9.0 | 9.0 | 8.7 | 8.8 | 8.8 | 9.0 |
| | .250 | 9.0 | 9.0 | 9.0 | 9.0 | 9.0 | 9.0 | 8.8 | 8.8 | 8.8 | 9.0 |
| | .125 | 8.6 | 9.0 | 9.0 | 9.0 | 9.0 | 9.0 | 9.0 | 8.6 | 8.8 | 9.0 |
| (+)-2-(5-Isopropyl-5-methyl-4-oxo-2-imidazolin-2-yl)-nicotinic acid | .500 | 9.0 | | 9.0 | 9.0 | 9.0 | 9.0 | 9.0 | 9.0 | 9.0 | 9.0 |
| | .250 | 9.0 | | 9.0 | 9.0 | 9.0 | 9.0 | 9.0 | 9.0 | 9.0 | 9.0 |
| | .125 | 9.0 | | 9.0 | 9.0 | 9.0 | 9.0 | 9.0 | 9.0 | 9.0 | 9.0 |
| 2-(5-Isopropyl-5-methyl-4-oxo-2-imidazolin-2-yl)-6-phenyl-nicotinic acid | 4.000 | 3.0 | 4.0 | 9.0 | 3.0 | 9.0 | 9.0 | 4.0 | 4.0 | 7.0 | |
| | 1.000 | 2.0 | 4.0 | 9.0 | 9.0 | 9.0 | 9.0 | 4.0 | 6.0 | 6.0 | |
| | .500 | 2.0 | 4.0 | 9.0 | | 9.0 | 9.0 | | | 5.0 | |
| 2-(5-Isopropyl-5-methyl-4-oxo-2-imidazolin-2-yl)-6-methyl-nicotinic acid | 4.000 | 9.0 | 9.0 | 9.0 | 9.0 | 9.0 | 9.0 | 9.0 | 9.0 | 9.0 | |
| | 1.000 | 9.0 | 9.0 | 9.0 | 9.0 | 9.0 | 9.0 | 9.0 | 9.0 | 9.0 | |
| | .500 | 9.0 | 9.0 | 9.0 | 9.0 | 9.0 | 9.0 | 9.0 | 9.0 | 9.0 | |
| | .250 | 9.0 | 9.0 | 9.0 | 9.0 | 9.0 | 9.0 | 9.0 | 9.0 | 9.0 | |
| 2-(5-Isopropyl-5-methyl-4-thiono-2-imidazolin-2-yl)nicotinic acid | .500 | 9.0 | 9.0 | 9.0 | 9.0 | 9.0 | 9.0 | 9.0 | 9.0 | 9.0 | |
| | .250 | 8.0 | 9.0 | 9.0 | 9.0 | 9.0 | 9.0 | 9.0 | 7.0 | 9.0 | |
| | .125 | 7.0 | 9.0 | 9.0 | 9.0 | 9.0 | 9.0 | 9.0 | 4.0 | 9.0 | |
| 6-Ethyl-2-(5-isopropyl-5-methyl-4-oxo-2-imidazolin-2-yl)nicotinic acid | .500 | 9.0 | | 9.0 | 8.0 | 9.0 | 9.0 | 9.0 | 9.0 | 9.0 | |
| | .250 | 9.0 | | 9.0 | 7.0 | 9.0 | 9.0 | 9.0 | 9.0 | 8.0 | |
| | .125 | 6.0 | | 9.0 | 7.0 | 9.0 | 9.0 | 9.0 | 9.0 | 7.0 | |
| 2-(5-Isopropyl-5-methyl-4-oxo-2-imidazolin-2-yl)-6-propylnicotinic acid | .250 | 4.0 | | 8.0 | 5.0 | 8.0 | 9.0 | 7.0 | 6.0 | 7.0 | |
| | .125 | 4.0 | | 8.0 | 5.0 | 4.0 | 8.0 | 5.0 | | 4.0 | |
| 2-(5-Isopropyl-5-methyl-4-oxo-2-imidazolin-2-yl)-6-p-tolyl-nicotinic acid | .500 | 8.0 | | 6.0 | 4.0 | 9.0 | 4.0 | 8.0 | 0.0 | 6.0 | |
| | .250 | 2.0 | | 3.0 | 1.0 | 4.0 | 3.0 | 3.0 | 0.0 | 3.0 | |
| | .125 | 0.0 | | 1.0 | 0.0 | 2.0 | 1.0 | 1.0 | 0.0 | 2.0 | |

| Compound | RATE | CORN FIELD | RICE, NATO | SOYBEAN WI | SUNFLR XXX | S WHEAT ER |
|---|---|---|---|---|---|---|
| 2-(5-Isopropyl-5-methyl-4-oxo-2-imidazolin-2-yl)-nicotinic acid | 10.000 | | | | | |
| | 2.000 | 9.0 | 9.0 | 8.0 | | |
| | 1.000 | 9.0 | 9.0 | 8.5 | 9.0 | 9.0 |
| | .500 | 9.0 | 9.0 | 8.7 | 9.0 | 9.0 |
| | .250 | 9.0 | 9.0 | 8.7 | 9.0 | 9.0 |
| | .125 | 9.0 | 9.0 | 8.7 | 9.0 | 9.0 |
| (+)-2-(5-Isopropyl-5-methyl-4-oxo-2-imidazolin-2-yl)-nicotinic acid | .500 | 9.0 | 9.0 | | 9.0 | 9.0 |
| | .250 | 9.0 | 9.0 | | 9.0 | 9.0 |
| | .125 | 9.0 | 9.0 | | 9.0 | 9.0 |
| 2-(5-Isopropyl-5-methyl-4-oxo-2-imidazolin-2-yl)-6-phenyl-nicotinic acid | 4.000 | 9.0 | 7.0 | | 9.0 | 5.0 |
| | 1.000 | 9.0 | 5.0 | | 9.0 | 5.0 |
| | .500 | | | | 9.0 | 5.0 |
| 2-(5-Isopropyl-5-methyl-4-oxo-2-imidazolin-2-yl)-6-methyl-nicotinic acid | 4.000 | 9.0 | 9.0 | | 9.0 | 9.0 |
| | 1.000 | 9.0 | 9.0 | | 9.0 | 9.0 |
| | .500 | 9.0 | 9.0 | | 9.0 | 9.0 |
| | .250 | 9.0 | 9.0 | | 9.0 | 9.0 |
| 2-(5-Isopropyl-5-methyl-4-thiono-2-imidazolin-2-yl)nicotinic acid | .500 | 9.0 | 9.0 | 9.0 | 9.0 | 9.0 |
| | .250 | 9.0 | 9.0 | 9.0 | 9.0 | 9.0 |
| | .125 | 9.0 | 9.0 | 8.0 | 9.0 | 9.0 |
| 6-Ethyl-2-(5-isopropyl-5-methyl-4-oxo-2-imidazolin-2-yl)nicotinic acid | .500 | 9.0 | 9.0 | | 9.0 | 9.0 |
| | .250 | 9.0 | 9.0 | | 9.0 | 7.0 |
| | .125 | 9.0 | 8.0 | | 8.0 | 7.0 |
| 2-(5-Isopropyl-5-methyl-4-oxo-2-imidazolin-2-yl)-6-propylnicotinic acid | .250 | 6.0 | 9.0 | | 6.0 | 4.0 |
| | .125 | 6.0 | 9.0 | | 3.0 | 4.0 |
| 2-(5-Isopropyl-5-methyl-4-oxo-2-imidazolin-2- | .500 | 7.0 | 5.0 | 6.0 | 7.0 | 2.0 |
| | .250 | 2.0 | 3.0 | 5.0 | 6.0 | 1.0 |
| | .125 | 2.0 | 1.0 | 4.0 | 3.0 | 0.0 |

I claim:
1. A process for the preparation of a compound of formula:

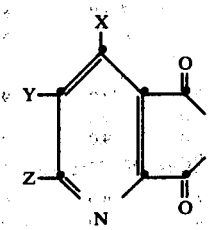

wherein X is hydrogen, halogen or methyl, with the proviso that when Y and Z are taken together to form a ring and YZ is represented by the structure: —(CH$_2$)$_n$—, where n is 3 or 4, then X is hydrogen; Y and Z each are hydrogen, halogen, C$_1$-C$_6$ alkyl, C$_1$-C$_6$ alkoxy, C$_1$-C$_4$ alkylthio, phenoxy, C$_1$-C$_4$ haloalkyl, nitro, cyano, C$_1$-C$_4$ alkylsulfonyl group, or phenyl optionally substituted with one C$_1$-C$_4$ alkyl, C$_1$-C$_4$ alkoxy or halogen; and, when taken together, Y and Z may form a ring in which —(YZ)— is represented by the structure: —(CH$_2$)$_n$—, where n is an integer selected from 3 and 4, provided that X is hydrogen; or

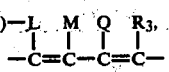

where L, M, Q and R$_3$ are each hydrogen, halogen, C$_1$-C$_4$ alkyl, C$_1$-C$_4$ alkoxy, C$_1$-C$_4$ alkylthio, C$_1$-C$_4$ alkylsulfonyl, C$_1$-C$_4$ haloalkyl, NO$_2$, CN, phenyl, phenoxy, chlorophenyl, methylphenyl, or phenoxy substituted with one Cl, CF$_3$, NO$_2$ or CH$_3$ group, with the proviso that only one of L, M, Q or R$_3$, may represent a substituent other than hydrogen, halogen, C$_1$-C$_4$ alkyl or C$_1$-C$_4$ alkoxy; comprising: reacting one molar equivalent of a compound of formula:

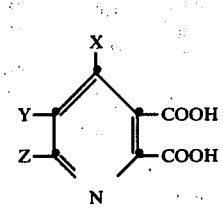

wherein X, Y and Z are as hereinabove defined, with from 1 to 6 molar equivalents of phosgene in the presence of a solvent of aliphatic and aromatic hydrocarbons, alkylnitriles, ethers or mixtures thereof; and in the presence of from 0.05 molar equivalent to 0.75 molar equivalent of dimethylformamide, at a temperature range of from —5° C. to +50° C. for a period of time sufficient to essentially complete the reaction.

2. The process according to claim 1, wherein the amount of phosgene is 1 to 2 molar equivalents; the amount of dimethylformamide is 0.2 to 0.4 molar equivalent; the temperature range is from +15° C. to +25° C.; the time is from 2 hours to 5 hours.

3. The process according to claim 1, wherein X is hydrogen; Y is hydrogen or methyl; Z is hydrogen, methyl, ethyl, propyl, isopropyl, trifluoromethyl, p-tolyl or p-chlorophenyl; or X is hydrogen and —(YZ)— is

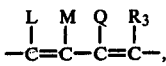

and L, M, Q and R$_3$ are as defined in claim 1.

4. The process according to claim 1, wherein one molar equivalent of pyridine-2,3-dicarboxylic acid is reacted with 1 to 2 molar equivalents of phosgene in the presence of 0.32 molar equivalents of dimethylformamide, acetonitrile and/or toluene, at a temperature of +15° C. to +25° C. for a period of time of from 2 to 5 hours, or until the reaction is essentially complete.

5. The process according to claim 4, wherein the compound is prepared from quinoline-2,3-dicarboxylic acid.

* * * * *